(12) United States Patent
Benicewicz et al.

(10) Patent No.: US 9,359,453 B2
(45) Date of Patent: Jun. 7, 2016

(54) PHOSPHONATE AND PHOSPHONIC ACID RAFT AGENTS AND MONOMERS, ALONG WITH METHODS OF THEIR MANUFACTURE AND USE

(71) Applicants: Brian Benicewicz, Columbia, SC (US); Anand Viswanath, Columbia, SC (US); Alexandra Nicole Green, Columbia, SC (US)

(72) Inventors: Brian Benicewicz, Columbia, SC (US); Anand Viswanath, Columbia, SC (US); Alexandra Nicole Green, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/484,990

(22) Filed: Sep. 12, 2014

(65) Prior Publication Data
US 2015/0073109 A1    Mar. 12, 2015

Related U.S. Application Data

(60) Provisional application No. 61/877,027, filed on Sep. 12, 2013.

(51) Int. Cl.
| C08F 2/38 | (2006.01) |
| C07C 329/00 | (2006.01) |
| C07F 9/40 | (2006.01) |
| C07F 9/38 | (2006.01) |

(52) U.S. Cl.
CPC ............... *C08F 2/38* (2013.01); *C07C 329/00* (2013.01); *C07F 9/3808* (2013.01); *C07F 9/4006* (2013.01); *C08F 2438/03* (2013.01)

(58) Field of Classification Search
CPC ....... C08F 2/38; C07C 329/00; C07F 9/4006; C07F 9/3808
USPC ............. 524/80; 526/193; 560/147; 562/426; 558/180
See application file for complete search history.

(56) References Cited

PUBLICATIONS

Chapman et al. "Multi-shell Soft Nanotubes from Cyclic Peptide Templates", Advanced Materials, 2013, 25, 1170-1172.*
Bhattacharjee et al. "Protein-Polymer Grafts via a Soy Protein Derived Macro-RAFT Chain Transfer Agent", J. Polym Environ. (2011) 19, pp. 203-208.*
Rieger et al. "Surfactant-Free RAFT Emulsion Polymerization Using Poly(N,N-dimethylacrylamide) Trithiocarbonate Macromolecular Chain Transfer Agents", Macromolecules 2010, 43, 6302-6310.*

* cited by examiner

*Primary Examiner* — Michael M Bernshteyn
(74) *Attorney, Agent, or Firm* — Dority & Manning, P.A.

(57) ABSTRACT

An intermediate compound for forming a RAFT agent is provided that can have the formula:

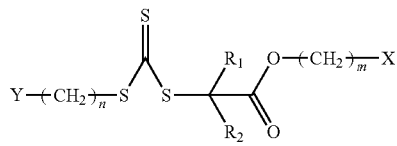

where $n$ is an integer from 1 to 20; $m$ is an integer from 0 to 20; $R_1$ is H, an alkyl group, or a cyano group; $R_2$ is H, an alkyl group, or a cyano group; Y is OH, COOH, or $NH_2$; and X is OH, COOH, $NH_2$, a nitrobenzyl, benzyl, or para-methyl benzyl group. A RAFT agent is also provided that comprises a thiocarbonylthio-containing organic compound having a phosphonic end group. A method is also provided for forming a polymer chain on a surface of a nanoparticle utilizing the RAFT agent, along with nanoparticles and nanocomposites formed therefrom.

9 Claims, 1 Drawing Sheet

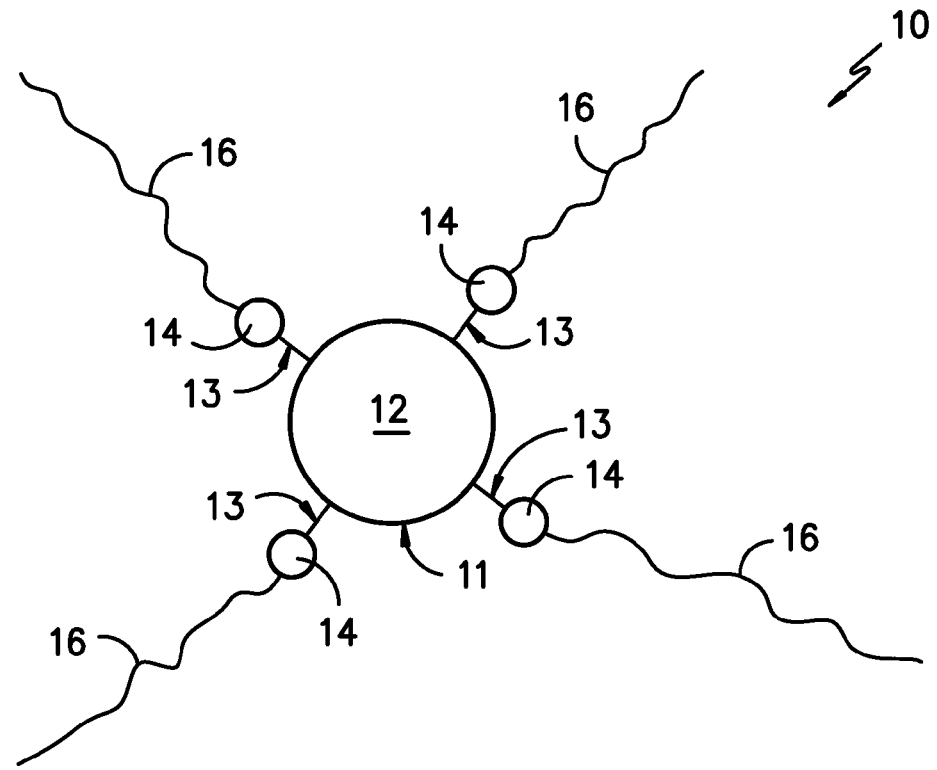
FIG. -1-
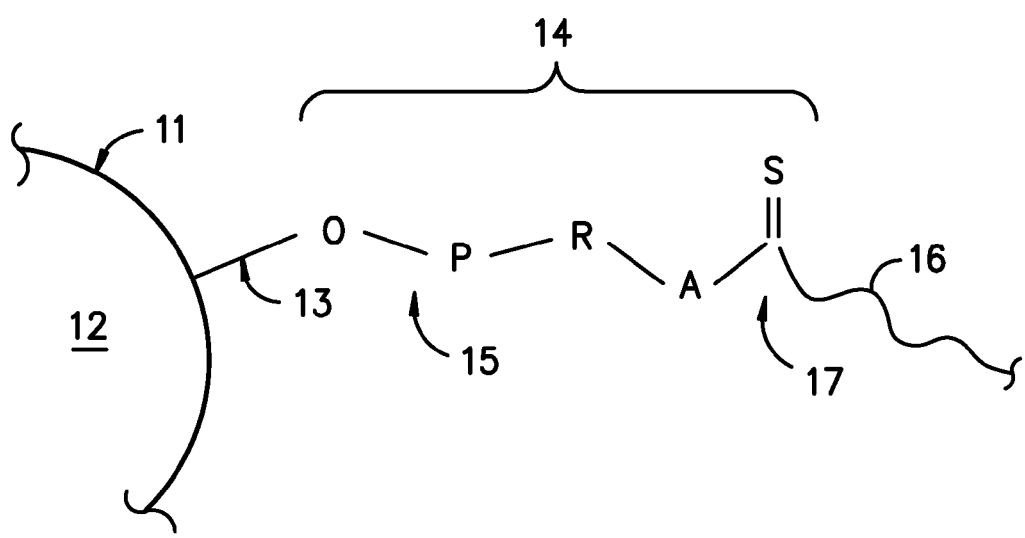
FIG. -2-

PHOSPHONATE AND PHOSPHONIC ACID RAFT AGENTS AND MONOMERS, ALONG WITH METHODS OF THEIR MANUFACTURE AND USE

PRIORITY INFORMATION

The present application claims priority to U.S. Provisional Patent Application Ser. No. 61/877,027 titled "Novel Phosphonate and Phosphonic Acid RAFT Agents and Monomers, Along with Methods of Their Manufacture and Use" of Benicewicz, et al. filed on Sep. 12, 2013, the disclosure of which is incorporated by reference herein.

FIELD OF THE INVENTION

Novel RAFT agents and monomers are generally provided, along with their methods of manufacture and use.

BACKGROUND

Polymer coated nanomaterials are useful in many applications, including in LEDs and bioimaging systems. However, the commercial usage of nanomaterials is limited by the poor optical and mechanical properties of the composite when the nanomaterial and polymer are blended together, which typically results in opaque films that have poor mechanical properties and are filled with aggregates (clumps of nanomaterials). For example, in LED device applications, high refractive index nanomaterials are in high demand as they would allow more light to be emitted with the same power input.

Nanomaterial functionalization is an exquisite process where particles have to be covered with polymers uniformly and via an easy process for any usage. This process provides a simple and versatile method to functionalize different nanomaterials including clays, alumina, $TiO_2$, CdSe etc. This process provides several methods of achieving polymer functionalization, including grafting-to, grafting-from and grafting-through techniques. Additionally, this process eliminates several expensive steps that are currently in use, which would facilitate mass production of such nanocomposites for optical applications. Typically, commercial nanocomposites have refractive indexes (RIs) from 1.3-1.5.

As such, a need exists for highly transparent and robust nanocomposites using polymers with special anchor points that bind extremely well with the nanomaterial.

SUMMARY

Objects and advantages of the invention will be set forth in part in the following description, or may be obvious from the description, or may be learned through practice of the invention.

An intermediate compound is, in one embodiment, generally provided for forming a RAFT agent. The intermediate compound can have the formula:

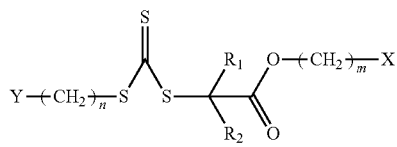

where n is an integer from 1 to 20 (e.g., 2 to 10); m is an integer from 0 to 20 (e.g., 2 to 10); $R_1$ is H, an alkyl group, or a cyano group; $R_2$ is H, an alkyl group, or a cyano group; Y is OH, COOH, or $NH_2$; and X is OH, COOH, $NH_2$, a nitrobenzyl, benzyl, or para-methyl benzyl group. Salts of such intermediate compounds are also generally provided.

A RAFT agent is, in one embodiment, generally provided that comprises a thiocarbonylthio-containing organic compound having a phosphonic end group. For example, the RAFT agent can have the formula:

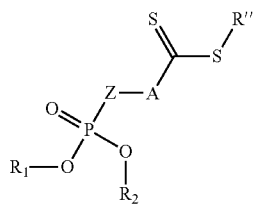

where Z is an organic linkage; $R_1$ is H or an alkyl group; $R_2$ is H or an alkyl group; A is O, S, or NH; and R" is an organic end group. For instance, R" can comprise an alkyl group terminating with a phenyl end group or a nitrophenyl end group, and/or may comprise a benzyl group, a nitrobenzyl group, or a para-methyl benzyl group. In one particular embodiment, the RAFT agent can have the formula:

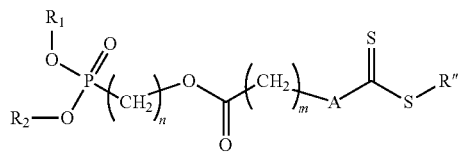

where n is 1 to 10 (e.g., 1-6), m is 1 to 10 (e.g., 1 to 6), $R_1$ is H or an alkyl group; $R_2$ is H or an alkyl group; A is O, S, or NH; and R" is an organic end group. Salts of the RAFT agents are also generally provided.

A method is also generally provided for forming a polymer chain on a surface of a nanoparticle. In one embodiment, the method can include: attaching a RAFT agent disclosed herein to the surface of the nanoparticle such that the phosphonic group of the RAFT agent is covalently bonded to the surface of the nanoparticle; and attaching a polymer to the RAFT agent (e.g., via a grafting-to method or a grafting-from method).

A nanocomposite is also generally provided that, in one embodiment, comprises a nanoparticle defining a surface, a RAFT agent attached to the surface of the nanoparticle, and a polymer attached to the RAFT agent. Generally, the RAFT agent comprises a thiocarbonylthio-containing organic compound having a phosphonic end group (such as discussed above) that is covalently bonded to the surface of the nanoparticle.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which:

FIG. 1 shows an exemplary nanocomposite according to one particular embodiment of the present invention; and FIG. 2 shows a close-up view of the nanocomposite to show the attachment between the surface of the nanoparticle and the polymer via the RAFT agent, according to one particular embodiment of the present invention.

Repeat use of reference characters in the present specification and drawings is intended to represent the same or analogous features or elements of the present invention.

DEFINITIONS

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the prefix "nano" refers to the nanometer scale (e.g., from about 1 nm to about 999 nm). For example, particles having an average diameter on the nanometer scale (e.g., from about 1 nm to about 999 nm) are referred to as "nanoparticles". Particles having an average diameter of greater than 1,000 nm (i.e., 1 μm) are generally referred to as "microparticles", since the micrometer scale generally involves those materials having an average size of greater than 1 μm.

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

The polydispersity index (PDI) is a measure of the distribution of molecular mass in a given polymer sample. The PDI calculated is the weight average molecular weight divided by the number average molecular weight. It indicates the distribution of individual molecular masses in a batch of polymers. The PDI has a value equal to or greater than 1, but as the polymer chains approach uniform chain length, the PDI approaches unity (i.e., 1).

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally speaking, novel RAFT agents are presently disclosed that have unique synthetic routes and polymers with novel binding points to inorganic materials. In particular embodiments, the RAFT agents are provided that include a phosphonate or phosphonic acid functional group that can attach to various inorganic materials to get high refractive index polymers. The novel RAFT agents outlined herein facilitate the development of polymers with phosphonic acid/phosphate end groups that can be used to attach with a variety of nanomaterials.

I. RAFT Polymerization

Reversible Addition-Fragmentation chain Transfer (RAFT) polymerization is one type of controlled radical polymerization. RAFT polymerization uses thiocarbonylthio compounds, such as dithioesters, dithiocarbamates, trithiocarbonates, and xanthates, in order to mediate the polymerization via a reversible chain-transfer process. RAFT polymerization can be performed by simply adding a chosen quantity of appropriate RAFT agents (thiocarbonylthio compounds) to a conventional free radical polymerization. RAFT polymerization is particularly useful with monomers having a vinyl functional group (e.g., a (meth)acrylate group).

Typically, a RAFT polymerization system includes the monomer, an initiator, and a RAFT agent (also referred to as a chain transfer agent). Because of the low concentration of the RAFT agent in the system, the concentration of the initiator is usually lower than in conventional radical polymerization. Suitable radical initiators can be azobisisobutyronitrile (AIBN), 4,4'-azobis(4-cyanovaleric acid) (ACVA), etc.

RAFT agents are generally thiocarbonylthio compounds, such as generally shown below:

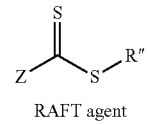

Formula 1

RAFT agent where the z group primarily stabilizes radical species added to the C=S bond and the R group is a good homolytic leaving group which is able to initiate monomers. The z and R" group of a RAFT agent is chosen according to a number of considerations. The z group primarily affects the stability of the S=C bond and the stability of the adduct radical (polymer-S—C.(Z)—S-polymer), which, in turn, affect the position of and rates of the elementary reactions in the pre- and main-equilibrium. The R" group stabilizes a radical such that the right hand side of the pre-equilibrium is favored, but remains unstable enough that it can reinitiate growth of a new polymer chain.

As stated, RAFT is a type of living polymerization involving a conventional radical polymerization in the presence of a reversible chain transfer reagent. Like other living radical polymerizations, there is minimized termination step in the RAFT process. The reaction is started by radical initiators (e.g., AIBN). In this initiation step, the initiator reacts with a monomer unit to create a radical species which starts an active polymerizing chain. Then, the active chain reacts with the thiocarbonylthio compound, which kicks out the homolytic leaving group (R"). This is a reversible step, with an intermediate species capable of losing either the leaving group (R") or the active species. The leaving group radical then reacts with another monomer species, starting another active polymer chain. This active chain is then able to go through the addition-fragmentation or equilibration steps. The equilibration keeps the majority of the active propagating species into the dormant thiocarbonyl compound, limiting the possibility of chain termination. Thus, active polymer chains are in equilibrium between the active and dormant species. While one polymer chain is in the dormant stage (bound to the thiocarbonyl compound), the other is active in polymerization.

By controlling the concentration of initiator and thiocarbonylthio compound and/or the ratio of monomer to thiocarbonylthio compound, the molecular weight of the polymeric chains can be controlled with low polydispersities.

Depending on the target molecular weight of final polymers, the monomer to RAFT agent ratios can range from about 10 to about 10,000 in particular embodiments. Other reaction parameters can be varied to control the molecular weight of the final polymers, such as solvent selection, reaction temperature, and reaction time. For instance, solvents can include conventional organic solvents such as tetrahydrofuran, toluene, dimethylformamide, anisole, acetonitrile, dichloromethane, etc. The reaction temperature can range from room temperature (e.g., about 20° C.) to about 120° C. The reaction time can be from less than about 1 h to about 48 h.

The RAFT process allows the synthesis of polymers with specific macromolecular architectures such as block, gradient, statistical, comb/brush, star, hyperbranched, and network copolymers.

Because RAFT polymerization is a form of living radical polymerization, it is ideal for synthesis of block copolymers. For example, in the copolymerization of two monomers (A and B) allowing A to polymerize via RAFT will exhaust the monomer in solution with significantly suppressed termination. After monomer A is fully reacted, the addition of monomer B will result in a block copolymer. One requirement for maintaining a narrow polydispersity in this type of copolymer is to have a chain transfer agent with a high transfer constant to the subsequent monomer (monomer B in the example).

II. Novel RAFT Agents

In order to synthesize phosphonic acid functionalized polymers, RAFT agents are provided that generally include a thiocarbonylthio-containing organic compound having a phosphonic end group. The phosphonic end group generally serves as an end group on the "z" group in the RAFT agent. While phosphonic acid end groups can be present on either the z or R" group, the following examples are focused on a phosphonic acid end group present as part of the z group. In one embodiment, the RAFT agent can be generally represented by the formula:

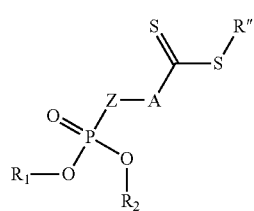

Formula 2 where Z is an organic linkage (with Z and the phosphonate group forming the z group discussed above); $R_1$ is H or an alkyl group (e.g., having a formula of $C_nH_{2n+1}$, with n being an integer of 1 to 6, such as 1 to 4); $R_2$ is H or an alkyl group (e.g., having a formula of $C_nH_{2n+1}$, with n being an integer of 1 to 6, such as 1 to 4); A is O, S, or NH; and R" is an organic end group that configured to cleave during the RAFT process and reinitiate the polymerization. In one particular embodiment, R" is an organic end group configured to affect the stability of the S=C bond and the stability of the adduct radical (polymer-S—C.(Z)—S-polymer). As such, the R" can be varied by changing the chemical composition of the organic group, and can be used to tailor the polydispersity of the resulting polymer. By changing the electron-donating or withdrawing nature of the R" group, the polydispersity can be tuned for the desired need in the application. The polydispersity can influence the mixing of the polymer-modified nanomaterial with the matrix polymer, and can have a significant effect on its physical and surface properties. In particular embodiments, R" includes a nitrobenzyl, benzyl, or para-methyl benzyl end group (either bonded directly to the thiocarbonyl group or via an alkyl group). As such, R" can, in one embodiment, include an alkyl group terminating with a nitrobenzyl, benzyl, or para-methyl benzyl end group.

Particularly suitable alkyl groups that can form $R_1$ and/or $R_2$ include methyl ($CH_3$), ethyl ($CH_2CH_3$), propyl ($CH_2CH_2CH_3$), iso-propyl ($CH(CH_3)_2$); butyl (e.g., $CH_2CH_2CH_2CH_3$), or tert-butyl ($C(CH_3)_3$).

In one embodiment, an ester group is included in the organic linkage of Z. For example, the organic linkage of Z can be an ethyl acetate linkage, which can be generally represented by the formula:

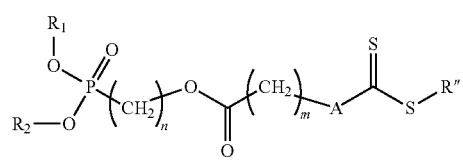

Formula 3 where n is 1 to 10 (e.g., 1-6), m is 1 to 10 (e.g., 1 to 6), $R_1$ is H or an alkyl group; $R_2$ is H or an alkyl group; A is O, S, or NH; and R" is an organic end group.

In particular embodiments, a phenyl group (serving as the z group in the RAFT agent) may be oppositely positioned from the phosphonic end group with the thiocarbonylthio group positioned between. The phenyl group may, in one particular embodiment, have an electron withdrawing group on its ring (e.g., at the para position), which can help control polymerization and, in turn, can lead to lower polydispersity of the resulting polymer. For example, a nitro functional group ($—NO_2$) can be positioned thereon (e.g., bonded to the phenyl ring at the para position).

A. Exemplary RAFT Agents

Particularly suitable RAFT agents for synthesizing phosphonic acid functionalized polymers have the formulas:

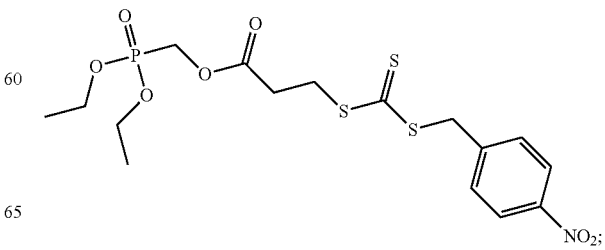

-continued

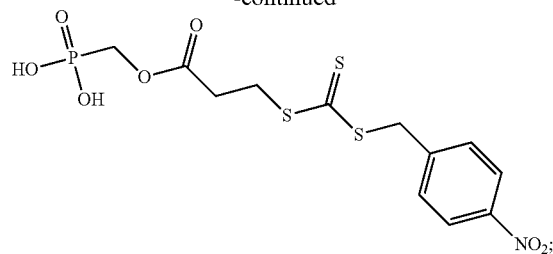

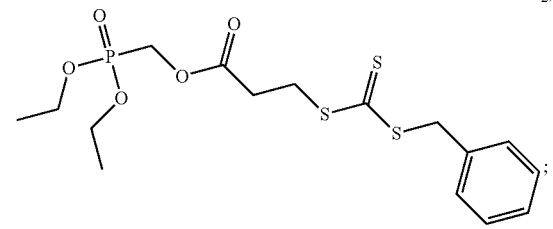

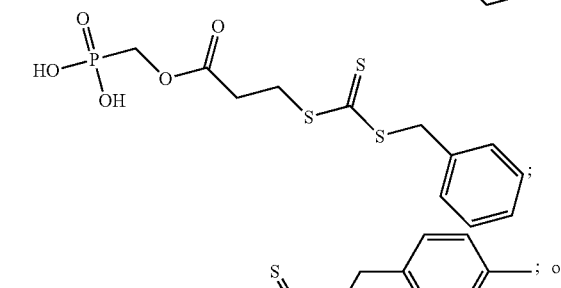

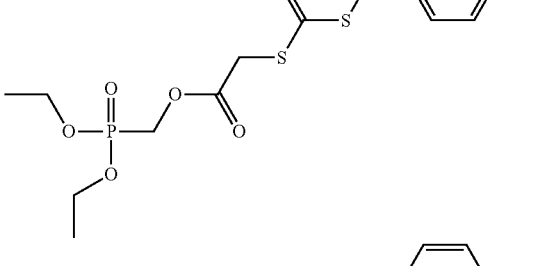

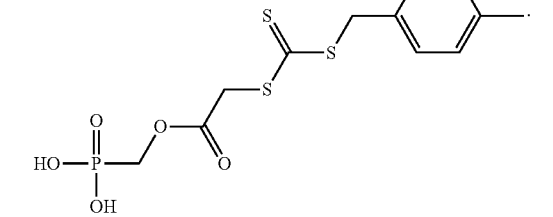

B. Intermediate Compounds

The RAFT agents described can be, in particular embodiments, formed from intermediate compounds such as the ones described below. In one embodiment, the intermediate compound has the formula:

Formula 4

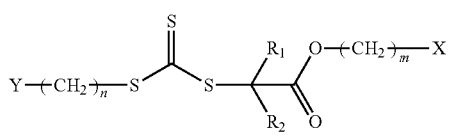

where n is an integer from 1 to 20 (e.g., about 2 to about 10); m is an integer from 0 to 20 (e.g., about 0 to about 10); $R_1$ is H, an alkyl group, or a cyano group; $R_2$ is H, an alkyl group, or a cyano group; Y is OH, COOH, or $NH_2$; and X is OH, COOH, $NH_2$, a nitrobenzyl, benzyl, or para-methyl benzyl group. In particular embodiments, the constituents $R_1$, $R_2$, and/or X and the value of n and m in the intermediate compound can translate, respectively, into the constituents $R_1$, $R_2$, and/or R" and the values of n and m of Formula 3.

Particularly suitable intermediate compounds can include, for example, compounds having the formulas:

III. Nanoparticles

The presently disclosed methods can be utilized on a variety of different types of nanoparticles. The nanoparticle may comprise, for example, natural or synthetic nanoclays (including those made from amorphous or structured clays), inorganic metal oxides (e.g., silica, alumina, and the like), nanolatexes, organic nanoparticles, etc. Particularly suitable nanoparticles include inorganic nanoparticles, such as silica, alumina, titania ($TiO_2$), indium tin oxide (ITO), CdSe, etc., or mixtures thereof. Suitable organic nanoparticles include polymer nanoparticles, carbon, graphite, graphene, carbon nanotubes, virus nanoparticles, etc., or mixtures thereof.

Nanoparticles as used herein means particles (including but not limited to rod-shaped particles, disc-shaped particles, platelet-shaped particles, tetrahedral-shaped particles), fibers, nanotubes, or any other materials having at least one dimension on the nano scale. In one embodiment, the nanoparticles have an average particle size of about 1 to about 1000 nanometers, preferably 2 to about 750 nanometers. That is, the nanoparticles have a dimension (e.g., a diameter or length) of about 1 to 1000 nm. Nanotubes can include structures up to 1 centimeter long, alternatively with a particle size from about 2 to about 50 nanometers. Due to their size, nanoparticles have very high surface-to-volume ratios.

The nanoparticles may be crystalline or amorphous. A single type of nanoparticle may be used, or mixtures of different types of nanoparticles may be used. If a mixture of nanoparticles is used they may be homogeneously or non-homogeneously distributed in the composite material or a system or composition containing the composite material. Non-limiting examples of suitable particle size distributions of nanoparticles are those within the range of about 2 nm to less than about 750 nm, alternatively from about 2 nm to less than about 200 nm, and alternatively from about 2 nm to less than about 150 nm.

It should also be understood that certain particle size distributions may be useful to provide certain benefits, and other ranges of particle size distributions may be useful to provide other benefits (for instance, color enhancement requires a different particle size range than the other properties). The average particle size of a batch of nanoparticles may differ from the particle size distribution of those nanoparticles. For example, a layered synthetic silicate can have an average particle size of about 25 nanometers while its particle size distribution can generally vary between about 10 nm to about 40 nm.

In one embodiment, the nanoparticles can be exfoliated from a starting material to form the nanoparticles. Such starting material may have an average size of up to about 50 microns (50,000 nanometers). In another embodiment, the nanoparticles can be grown to the desired average particle size.

IV. Attaching a Polymer to the Nanoparticle

The RAFT agents (discussed in section II above) are attached to the surface of the nanoparticle (discussed in section III above) for subsequent attachment/formation of a polymeric chain thereto (e.g., via a "grafting-to" or "grafting-from" approach, as described in greater detail below). That is, the RAFT agent can be covalently bonded directly to the surface of the nanoparticle via its phosphonate group.

Two methods can be utilized to form the polymeric chain extending from the nanoparticles via the attached RAFT agent: a "grafting-from" approach and a "grafting-to" approach. These strategies are explained in more details in the following sections. (See also, U.S. Publication No. 2013/0041112 of Benicewicz, et al.; U.S. Publication No. 2012/0302700 of Tao, et al.; and international patent application publication no. WO/2013/078309 of Benicewicz, et al., the disclosures of which are incorporated by reference herein.)

A. "Grafting-from" Methods

In one embodiment, the polymeric chain can be formed by RAFT polymerization of a plurality of monomers on the attached RAFT agent, resulting in the polymeric chain being covalently bonded to the nanoparticle via the RAFT agent. The particular types of monomer(s) and/or RAFT polymerization conditions can be selected based upon the desired polymeric chain to be formed. For example, monomers containing acrylate, methacrylate groups, acrylamides, styrenics, etc., are particularly suitable for formation of the polymeric chain.

Thus, the "grafting-from" method involves formation of the polymeric chain onto the attached RAFT agent and results in the polymeric chain being covalently bonded to the nanoparticle via the attached RAFT agent.

B. "Grafting-to" Methods

In one embodiment, the polymeric chain can be first polymerized via RAFT polymerization with the RAFT agent of section II above and subsequently covalently bonded directly to the surface of the nanoparticle, via its phosphonate end group. Thus, in this embodiment, the polymeric chain has been polymerized prior to attachment to the nanoparticle's surface.

Alternatively, the polymeric chain can be first polymerized and subsequently covalently bonded to the surface of the nanoparticle, via a RAFT agent of section II attached directly to the surface of the nanoparticle. Thus, in this embodiment, the first polymeric chain has been polymerized prior to attachment to the first anchoring compound. In this embodiment, the first polymeric chain is not limited to the type of polymerization and/or types of monomer(s) capable of being polymerized directly to the attached RAFT agent. As such, as long as the polymeric chain defines a functional group that can react and bond to the attached RAFT agent, any polymeric chain can be bonded to the nanoparticle.

V. Nanocomposites

Through these methods, nanocomposites can be formed having a polymer chain attached to the surface of a nanoparticle (of section III above) via a phosphonate/phosphonic acid group of a RAFT agent (as in section II above). FIG. 1 shows an exemplary nanocomposite 10 that includes a nanoparticle 12 defining a surface 11. A RAFT agent 14 is attached directly to the surface 11 via a covalent bond 13. A polymer 16 is attached to RAFT agent 14. As shown, multiple RAFT agents 14 and polymers 16 can be attached to the nanoparticle 12 to form the nanocomposite 10.

For example, as shown in the close-up view of FIG. 2, the phosphonate group 15 of the RAFT agent 14 can be covalently bonded to the surface 11 of the nanoparticle 12, while the polymer chain 16 can be covalently bonded to the thiocarbonyl group 17 of the RAFT agent 14.

In one particular embodiment, a nanocomposite can be formed from $TiO_2$ nanoparticles to increase their refractive index. The refractive index (RI) of $TiO_2$ ranges from 2.4-2.6. However, with the incorporation of polymers with phosphonic acids to $TiO_2$ nanoparticles, higher RI nanocomposites can be obtained, such as up to 1.8 (e.g., about 1.2 to about 1.8, such as about 1.5 to about 1.8).

EXAMPLES

In order to synthesize phosphonic acid functionalized polymers, RAFT agents were designed using a carboxylic acid functionalized thiol. After the thiol is reacted with carbon disulfide to form a trithiocarbonate, the carboxylic acid end can be utilized to react with a hydroxy phosphonate. The resulting novel phosphonate trithiocarbonate can be deprotected to the phosphonic acid trithiocarbonate to graft directly to $TiO_2$ nanoparticles for the 'grafting-from' technique. Alternatively, the phosphonate trithiocarbonate can be polymerized with a variety of monomers to get phosphonate functionalized polymers. These polymers can be deprotected to get the phosphonic acid polymer for the 'grafting-to' technique.

Furthermore, an alternative approach for the purpose of multiple phosphonic acid binding sites was to use phosphonic acid based monomers. Methacrylate based phosphonate monomers were synthesized using the hydroxy phosphonate and methacryloyl chloride. Such polymers with the multiple binding sites were attached with $TiO_2$ to form novel nanocomposite systems.

Experimental: Section 1

Dithiodipropionic acid (2.38 mmol) was added to a round bottom flask with DCM (10 mL) and THF (5 mL). Diethyl hydroxyl phosphate (6.66 mmol) was added to the solution followed by DMAP (2.38 mmol). In a separate vial DCC (6.90 mmol) was dissolved in THF (2 mL). The DCC solution was added drop-wise under stirring in an ice bath. The mixture was flushed with Nitrogen and stirred at ambient temperature for 28 hours.

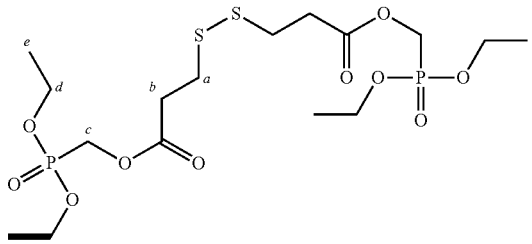
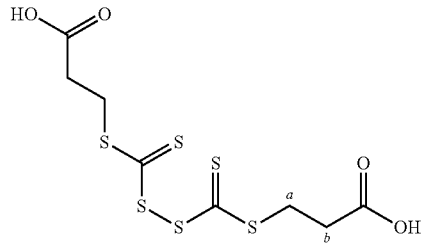

¹H NMR (300 MHz, CDCl₃), δ (ppm form TMS): 1.35 (t, 3H), 2.8 (t, 2H), 2.9 (t, 2H), 4.1-4.3 (q, 2H), 4.4 (d, 2H)

¹³C NMR: 16 (CH₃—CH₂), 32 (COOH—CH₂—CH₂), 34 (COOH—CH₂—CH₂), 62 (CH₃—CH₂), 171 (COOH—CH₂—CH₂)

Experimental: Section 2

Diethyl Ether (10 mL) and TEA (2.77 mL, 19.88 mmol) were added to a round bottom flask. 3-mercaptopropionic acid (9.42 mmol) was added drop-wise under stirring in an ice bath. Carbon Disulfide (0.87 mL, 14.42 mmol) was added drop-wise under stirring in an ice bath. Solution was kept under ice for one hour then ambient temperature for another hour. The solvent was then removed by filtration and washed 3 times with diethyl ether to eliminate excess TEA and Carbon Disulfide.

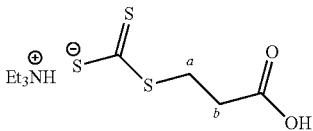

¹H NMR (300 MHz, CDCl₃), δ (ppm form TMS): 1.2 (TEA), 2.5 (t, 2H), 2.7 (t, 2H), 2.9 (TEA).

A suspension was made in diethyl ether. Solid Iodine (0.21 mmol) was added in portions and the mixture stirred for 1 hour at room temperature. Sodium Iodide was removed by filtration. The yellow brown filtrate was washed with aqueous sodium thiosulfate and dried over anhydrous sodium sulfate.

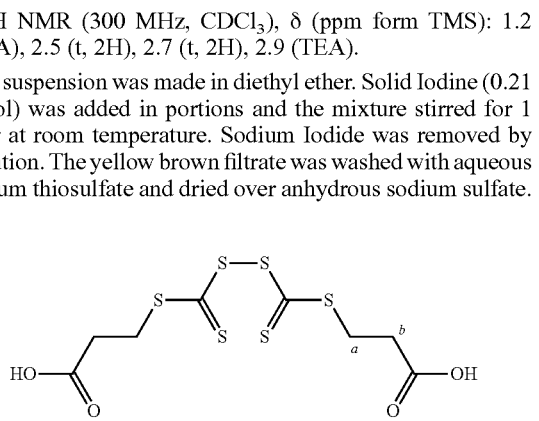

¹H NMR (300 MHz, CDCl₃), δ (ppm form TMS): 2.9 (t, 2H), 3.1 (t, 2H).

Experimental: Section 3

3-mercaptopropionic acid (9.42 mmol) added drop-wise to potassium hydroxide solution in water. Aliquat 336 and Carbon Disulfide mixture (0.57 mL, 9.42 mmol) was added. Solution stirred for 30 minutes at ambient temperature. The solution was cooled to −5° C. in a salt water solution. 4-Toluenesulfonyl chloride (TsCl) (4.71 mmol) was added in small portions over 5 minutes and stirred at ambient temperature for one hour. The solution was then heated to 45° C. and stirred for 10 minutes. Product was washed with water and recrystallized with acetone.

¹H NMR (300 MHz, CDCl₃), δ (ppm form TMS): 2.8 (t, 2H), 2.95 (t, 2H).

¹³C NMR (75 MHz, CDCl₃), δ (ppm form TMS): 33 (COOH—CH₂—CH₂), 34 (COOH—CH₂—CH₂).

Mass: Major peak at 228.

Experimental: Section 4

3-mercaptopropionic acid (9.42 mmol) was mixed with dichloromethane (DCM) (10.2 mL) and the solution was stirred for 10 minutes at ambient temperature. Triethylamine (TEA) (1.31 mL, 9.42 mmol) was added then carbon disulfide (0.76 mL, 12.62 mmol) was added drop-wise under stirring in an ice bath. The solution was stirred for 5 hours at ambient temperature. Solvent was partially evaporated under vacuum. Product precipitated in ether three times and the orange oil was separated from ether by evaporation under vacuum.

Nitrobenzylbromide (9.42 mmol) was dissolved in DCM (1.6 mL). Solution was stirred with 3-proprionicacidtrithiocarbonate salt for 16 hours at ambient temperature. Nitrobenzylbromide was filtered off and washed with DCM (5 mL). The product was purified by extraction with water and washed twice with 5 mL of 1M HCl in 95 mL water. The organic phase was dried with anhydrous sodium sulfate. The solvent was evaporated and yellow oil purified by a silica gel column (Hexanes/Ethyl acetate).

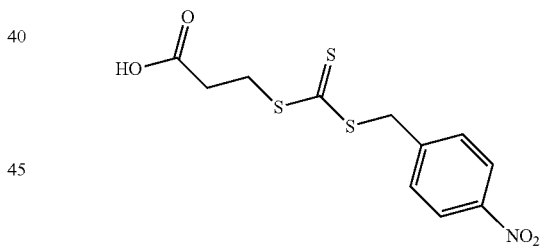

¹H NMR (300 MHz, CDCl₃), δ (ppm form TMS): 2.8 (t, 2H), 3.6 (t, 2H), 4.7 (s, 2H), 7.5 (d, 2H), 8.15 (d, 2H).

¹³C NMR (75 MHz, CDCl₃), δ (ppm form TMS): 32 (COOH—CH₂—CH₂), 38 (COOH—CH₂—CH₂), 48 (CH₂—C—CH—CH—C—NO₂), 124 (CH₂—C—CH—CH—C—NO₂), 130(CH₂—C—CH—CH—C—NO₂), 143 (CH₂—C—CH—CH—C—NO₂), 146 (CH₂—C—CH—CH—C—NO₂), 176 (COOH—CH₂—CH₂)

Mass: Major peak at 317.

Experimental: Section 5

Ethyl Disulfide diethyl phosphate (0.39 mmol) and water were dissolved in dimethylformamide (DMF) (3 mL) in a round bottom flask. The mixture was flushed with Nitrogen and Tributyl Phosphine (0.132 mL, 0.78 mmol) was added under Nitrogen. The solution was stirred for 1 hour at ambient temperature. DCM (10 mL) was added and the solution washed with water 3 times. The organic layer was rinsed with Sodium Sulfate and evaporation under vacuum.

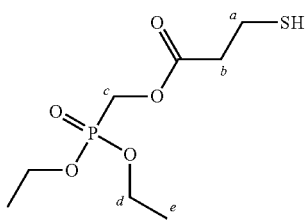

¹H NMR (300 MHz, CDCl₃), δ (ppm form TMS): 1.2-1.8 (t, 6H), 2.8 (t, 2H), 3.65 (t, 2H), 4.2-4.3 (d, 4H).

Experimental: Section 6

3-mercaptopropionic acid (9.42 mmol) was mixed with DCM (10.25 mL) and the solution was stirred for 10 minutes at ambient temperature. TEA (1.31 mL, 9.42d mmol) was added then Carbon Disulfide (0.76 mL, 12.62 mmol) was added drop-wise under stirring in an ice bath. The solution was stirred for 5 hours at ambient temperature. Solvent was partially evaporated under vacuum. Product precipitated in ether three times and the orange oil was separated from ether by evaporation under vacuum.

3-((((1-((6-hydroxyhexyl)oxy)-2-methyl-1-oxopropan-2-yl)thio)carbonothioyl)thio)propanoic acid (9.42 mmol) was dissolved in DCM (1.6 mL). Solution was stirred with 3-proprionicacidtrithiocarbonate salt for 16 hours at ambient temperature. Bromide was filtered off and washed with DCM (5 mL). The product was purified by extraction with water and washed twice with 5 mL of 1M HCl in 95 mL water. The organic phase was dried with anhydrous Sodium Sulfate. The solvent was evaporated and the yellow oil was purified by a silica gel column (Hexanes/Ethyl acetate).

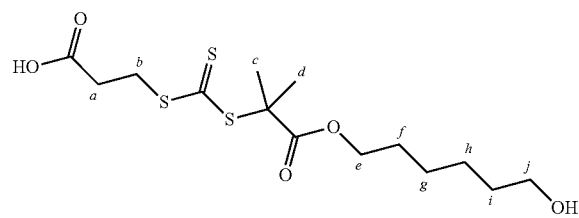 [SMILES: CC(C)(SC(=S)SCCC(=O)O)C(=O)OCCCCCCO]

¹H NMR (300 MHz, CDCl₃), δ (ppm form TMS): 1.4-2.1 (m, 8H) 1.6 (s, 6H), 2.8 (t, 2H), 3.6 (t, 2H), 3.65 (t, 2H), 4.2 (t, 2H)

¹³C NMR (75 MHz, CDCl₃), δ (ppm form TMS): 24.2 (S—CCH₃CH₃—COOH), 24.3 (S—CCH₃CH₃—COOH), 24.8 (CH₂—CH₂—CH₂—CH₂—CH₂—CH₂—OH), 24.9 (CH₂—CH₂—CH₂—CH₂—CH₂—CH₂-0H), 27 (CH₂—CH₂—CH₂—CH₂—CH₂—CH₂—OH), 31.5 (CH₂—CH₂—CH₂—CH₂—CH₂—CH₂—OH), 32 (COOH—CH₂—CH₂), 35 (COOH—CH₂—CH₂), 52 (S—CCH₃CH₃—COOH), 62 (CH₂—CH₂—CH₂—CH₂—CH₂—CH₂-0H), 65 (CH₂—CH₂—CH₂—CH₂—CH₂—CH₂—OH)

Mass: Major peak at 167

Experimental: Section 7

Potassium tert-butoxide (KOtBu) (9.42 mmol) and tetrahydrofuran (THF) (15 mL) were stirred for 30 minutes at ambient temperature. 3-mercaptopropionic acid (9.42 mmol) was added drop-wise under stirring in an ice bath. The solution was stirred for 30 minutes at ambient temperature. Carbon disulfide (0.336 mL, 9.73 mmol) was added drop-wise under stirring in an ice bath. The solution was stirred for 4 hours at ambient temperature. The solution was cooled to 15° C. and solid iodine (9.8 mmol) was added in small portions over 40 minutes. The mixture was stirred overnight and then filtered. The organic phase was washed with brine, sodium thiosulfate and followed with brine. The organic layer was dried with anhydrous Sodium Sulfate.

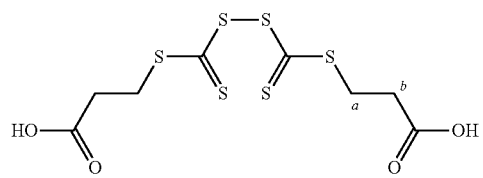 [SMILES: O=C(O)CCSC(=S)SSC(=S)SCCC(=O)O]

¹H NMR (300 MHz, CDCl₃), δ (ppm form TMS): 2.8 (t, 2H), 2.55 (t, 2H).

¹³C NMR (75 MHz, CDCl₃), δ (ppm form TMS): 32 (CS—CH₂—CH₂—COOH), 33 (CS—CH₂—CH₂—COOH), 175 (CS—CH₂—CH₂—COOH), 207 (CS—CH₂—CH₂—COOH)

Experimental: Section 8

3-mercaptopropionic acid (9.42 mmol) was mixed with DCM (10.2 mL) and the solution was stirred for 10 minutes at ambient temperature. TEA (1.31 mL, 9.42 mmol) was added, then carbon disulfide (0.76 mL, 12.62 mmol) was added drop-wise under stirring in an ice bath. The solution was stirred for 5 hours at ambient temperature. Solvent was partially evaporated under vacuum. Product precipitated in ether three times and the orange oil was separated from ether by rotary evaporation.

2-Bromoisobutyrophenone (0.19 mL, 1.13 mmol) was dissolved in chloroform (2 mL) and 3-propioicacidtrithiocarbonate salt (0.36 mL, 1.35 mmol) for 16 hours at 60° C. The bromide was filtered off and washed with DCM. The product was purified by extraction twice with water. The organic phase was dried with anhydrous sodium sulfate and the solvent was evaporated. Final yellow oil was purified by a silica gel column (Hexanes/Ethyl acetate).

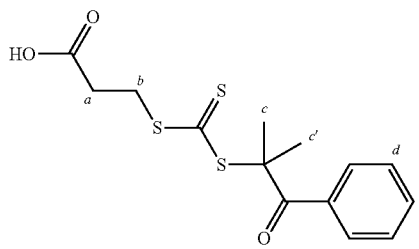 [SMILES: CC(C)(SC(=S)SCCC(=O)O)C(=O)c1ccccc1]

¹H NMR (300 MHz, CDCl₃), δ (ppm form TMS): 1.6 (s, 3H), 2.0 (s, 3H), 2.6 (t, 2H), 2H), 7.3-7.6 (m, 3H), 8.0-8.2 (d, 2H)

Experimental: Section 9

3-mercaptopropionic acid (9.42 mmol) was mixed with DCM (10.2 mL) and the solution was stirred for 10 minutes at ambient temperature. TEA (1.31 mL, 9.42 mmol) was added then carbon disulfide (0.76 mL, 12.62 mmol) was added drop-wise under stirring in an ice bath. The solution was stirred for 5 hours at ambient temperature. Solvent was partially evaporated under vacuum. Product precipitated in ether three times and the orange oil was separated from ether by evaporation under vacuum.

Benzyl bromide (0.347 mL, 2.92 mmol) was dissolved in DCM (3 mL) and stirred with 3-propionic acid trithiocarbonate salt (0.929 mL, 3.51 mmol) for 16 hours at ambient temperature. The bromide was filtered off and washed with DCM. The product was purified by extraction twice with water. The organic phase was dried with anhydrous sodium sulfate and the solvent was evaporated. The final yellow oil was purified with a silica gel column.

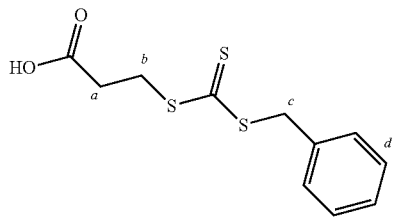 [SMILES: O=C(O)CCSC(=S)SCc1ccccc1]

$^1$H NMR (300 MHz, CDCl$_3$), δ (ppm form TMS): 2.8 (t, 2H), 3.6 (t, 2H), 4.6 (s, 2H), 7.2-7.4 (m, 5H)

Experimental: Section 10

3-mercaptopropionic acid (9.42 mmol) was mixed with DCM (10.2 mL) and the solution was stirred for 10 minutes at ambient temperature. TEA (1.31 mL, 9.42 mmol) was added then Carbon Disulfide (0.76 mL, 12.62 mmol) was added drop-wise under stirring in an ice bath. The solution was stirred for 5 hours at ambient temperature. Solvent was partially evaporated under vacuum. Product precipitated in ether three times and the orange oil was separated from ether by evaporation under vacuum.

Benzyl bromide (0.347 mL, 2.92 mmol) was dissolved in DCM (5 mL) and stirred with 3-propionic acid trithiocarbonate salt (0.36 mL, 1.35 mmol) for 16 hours at 60° C. attached to a condenser. The bromide was filtered off and washed with DCM. The product was purified by extraction twice with water. The organic phase was dried with anhydrous sodium sulfate and the solvent was evaporated. The final yellow oil was purified with a silica gel column (Hexanes/Ethyl acetate).

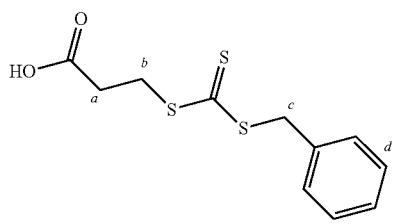 [SMILES: O=C(O)CCSC(=S)SCc1ccccc1]

$^1$H NMR (300 MHz, CDCl$_3$), δ (ppm form TMS): 2.8 (t, 2H), 3.6 (t, 2H), 4.5 (c', 2H), 4.6 (s, 2H), 7.2-7.4 (m, 5H)

Experimental: Section 11

3-mercaptopropionic acid (9.42 mmol) was mixed with DCM (10.2 mL) and the solution was stirred for 10 minutes at ambient temperature. TEA (1.31 mL, 9.42 mmol) was added then carbon disulfide (0.76 mL, 12.62 mmol) was added drop-wise under stirring in an ice bath. The solution was stirred for 5 hours at ambient temperature. Solvent was partially evaporated under vacuum. Product precipitated in ether three times and the orange oil was separated from ether by rotvap.

Alpha-bromo-p-xylene (1.13 mmol) was dissolved in DCM (2 mL) and stirred with 3-propionic acid trithiocarbonate salt (0.72 mL, 2.71 mmol) for 16 hours at 60° C. attached to a condenser. The bromide was filtered off and washed with chloroform. The product was purified by extraction twice with water. The organic phase was dried with anhydrous sodium sulfate and the solvent was evaporated. The final yellow oil was purified with a silica gel column (Hexanes/Ethyl acetate).

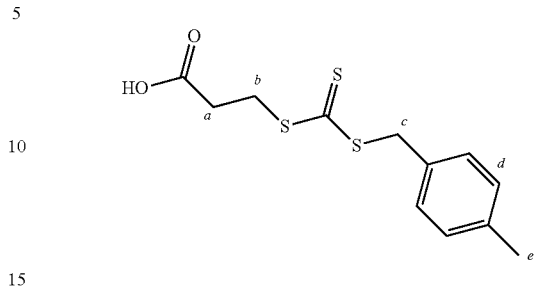

$^1$H NMR (300 MHz, CDCl$_3$), δ (ppm form TMS): 2.3 (s, 3H), 2.8 (t, 2H), 3.6 (t, 2H), 4.6 (s, 2H), 7.0-7.2 (d, 4H)

Experimental: Section 12

2-((((4-nitrobenzyl)thio)carbonothioyl)thio)acetic acid (NTCTPA) (0.945 mmol) was added to a round bottom flask and dissolved in DCM (10 mL). Diethyl hydroxy phosphate (0.859 mmol) was added followed by dimethylaminopyridine (DMAP) (0.172 mmol). In a separate vial N,N'-Dicyclohexylcarbodiimide (DCC) (0.945 mmol) was dissolved in DCM (2 mL). The DCC solution was added drop-wise under stirring in an ice bath. The flask was flushed with nitrogen and stirred for 28 hours at ambient temperature.

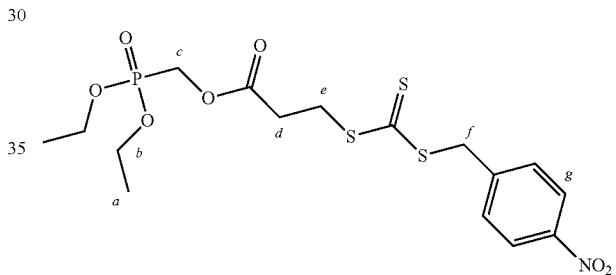

$^1$H NMR (300 MHz, CDCl$_3$), δ (ppm form TMS): 1.3 (t, 6H), 2.8 (t, 2H), 3.6 (t, 2H), 4.2 (q, 4H), 4.4 (d, 2H), 4.65 (s, 2H), 7.5 (d, 2H), 8.2 (d, 2H)

$^{13}$C NMR (75 MHz, CDCl$_3$), δ (ppm form TMS): 16 (CH$_3$—CH$_2$—P), 31 (COOH—CH$_2$—CH$_2$—S), 33 (COOH—CH$_2$—CH$_2$—S), 63 (CH$_3$—CH$_2$—P), 67 (P—CH$_2$—O), 124 (S—CH$_2$—C—CH—CH—C—NO$_2$), 130 (S—CH$_2$—C—CH—CH—C—NO$_2$)

$^{31}$P: 24

Mass: Major peak at 468.

Experimental: Section 13

3-mercaptopropionic acid (18.84 mmol) was mixed with DCM (20.5 mL) and the solution was stirred for 10 minutes at ambient temperature. Carbon disulfide (1.52 mL, 25.25 mmol) was added drop-wise under stirring in an ice bath. The solution was stirred for 5 hours at ambient temperature. Solvent was partially evaporated under vacuum. Product precipitated in ether three times and the orange oil was separated from ether by dimethylaminopyridine. Alpha-Bromo-p-xylene (9.42 mmol) was dissolved in chloroform (2 mL) and stirred with 3-propionic acid trithiocarbonate salt for 16 hours at 60° C. The bromide was filtered off and washed with chloroform. The product was purified by extraction twice with water. The organic phase was dried with anhydrous sodium sulfate and the solvent was evaporated. The final yellow oil was purified with a silica gel column.

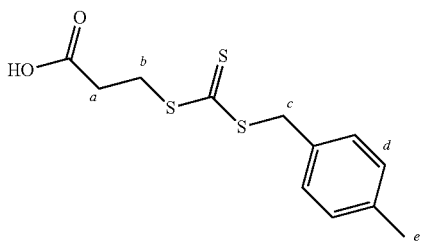 [SMILES: Cc1ccc(CSC(=S)SCCC(=O)O)cc1]

¹H NMR (300 MHz, CDCl₃), δ (ppm form TMS): 2.3 (s, 3H), 2.8 (t, 2H), 3.6 (t, 2H), 4.6 (s, 2H), 7.2-7.3 (d, 2H), 8.1 (d, 2H)

¹³C NMR (75 MHz, CDCl₃), δ (ppm form TMS): 22 (S—CH₂—C—CH—CH—C—CH₃), 31 (COOH—CH₂—CH₂—S), 33 (COOH—CH₂—CH₂—S), 41 (S—CH₂—C—CH—CH—C—CH₃), 128 (S—CH₂—C—CH—CH—C—CH₃), 129 (S—CH₂—C—CH—CH—C—CH₃), 132 (S—CH₂—C—CH—CH—C—CH₃), 138 (S—CH₂—C—CH—CH—C—CH₃), 176 (COOH—CH₂—CH₂—S)

Mass: Major peaks 105, 210 others 55, 76, 91, 137, 286

Experimental: Section 14

(diethoxyphosphoryl)methyl 2-((((4-nitrobenzyl)thio)carbonothioyl)thio)acetate (NTCTPA-diethyl phosphate) (0.205 mmol) was added to DCM (3 mL). Trimethylsilyl bromide (TMSBr) (0.108 mL, 0.205 mmol) was added to the solution drop-wise under nitrogen in an ice bath. The solution was stirred for 4 hours at ambient temperature then evaporated under vacuum. Methanol (3 mL) was added and the solution was stirred for 1 hour. The solution was evaporated under vacuum and recrystallized in 10% DCM/hexane solution.

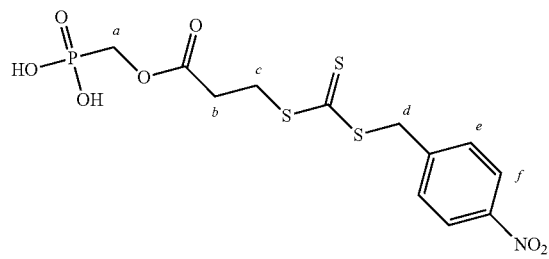 [SMILES: O=C(CCSC(=S)SCc1ccc([N+](=O)[O-])cc1)OCP(=O)(O)O]

¹H NMR (300 MHz, CDCl₃), δ (ppm form TMS): 2.8 (t, 2H), 3.6 (t, 2H), 4.4 (d, 2H), 4.65 (s, 2H), 7.5 (d, 2H), 8.2 (d, 2H)

³¹P: 19.22

Mass: Major peak: 449

Experimental: Section 15

3-mercaptopropionic acid (4.11 mL, 47.11 mmol) was mixed with DCM (20.5 mL) and TEA (6.57 mL, 47.11 mmol) and the solution was stirred for 10 minutes at ambient temperature. Carbon disulfide (3.82 mL, 63.12 mmol) was added drop-wise under stirring in an ice bath. The solution was stirred for 5 hours at ambient temperature. Solvent was partially evaporated under vacuum. Product precipitated in ether three times and the orange oil was separated from ether by evaporated under vacuum. Benzyl bromide (2.88 mL, 23.72 mmol) was dissolved in chloroform (20.5 mL) and stirred with 3-propionic acid trithiocarbonate salt for 16 hours at 60° C. The bromide was filtered off and washed with chloroform. The product was purified by extraction twice with water. The organic phase was dried with anhydrous sodium sulfate and the solvent was evaporated. The final yellow oil was purified with a silica gel column.

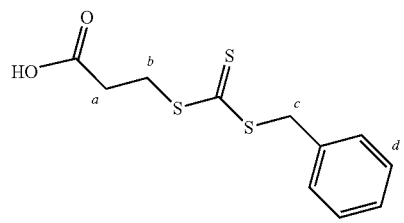 [SMILES: O=C(O)CCSC(=S)SCc1ccccc1]

¹H NMR (300 MHz, CDCl₃), δ (ppm form TMS): 2.89 (t, 2H), 3.6 (t, 2H), 4.6 (s, 2H), 7.2-7.4 (m, 5H)

Experimental: Section 16

Bis(trithiopropionic acid) (0.275 mmol) was dissolved in THF (4 mL) and degassed for 15 minutes. Recrystallized azobisisobutyronitrile (AIBN) (0.55 mmol) was added to a round bottom flask and attached to a condenser. The mixture was stirred at 80° C. overnight.

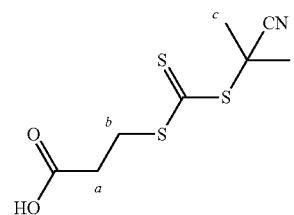

¹H NMR (300 MHz, CDCl₃), δ (ppm form TMS): 1.85 (s, 6H), 2.8 (t, 2H), 3.0 (t, 2H)

Experimental: Section 17

2-(((benzylthio)carbonothioyl)thio)acetic acid (BTCTPA) (3.67 mmol) was added to a round bottom flask and dissolved in DCM (30 mL). Diethyl hydroxy phosphate (0.48 mL, 3.34 mmol) was added followed by DMAP (0.67 mmol). In a separate vial DCC (3.67 mmol) was dissolved in DCM (6 mL) and the solution was added drop-wise under stirring in an ice bath. The flask was flushed with Nitrogen and stirred for 28 hours at ambient temperature.

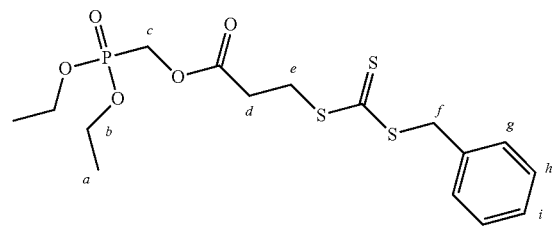 [SMILES: CCOP(=O)(COC(=O)CCSC(=S)SCc1ccccc1)OCC]

¹H NMR (300 MHz, CDCl₃), δ (ppm form TMS): 1.35 (t, 6H), 2.85 (t, 2H), 3.6 (t, 2H), 4.2 (q, 4H), 4.4 (d, 2H), 4.6 (s, 2H), 7.2-7.4 (m, 5H)

Experimental: Section 18

(diethoxyphosphoryl)methyl 2-(((benzylthio)carbonothioyl)thio)acetate (BTCTPA-diethyl phosphate) (0.136 mmol) was added to DCM (3 mL). TMSBr (0.54 mL, 0.409 mmol) was added to the solution drop-wise under Nitrogen in an ice bath. The solution was stirred for 4 hours at ambient temperature then rotovapped. Methanol (3 mL) was added and the solution was stirred for 1 hour. The solution was evaporated under vacuum and recrystallized in 10% DCM/Hexane solution.

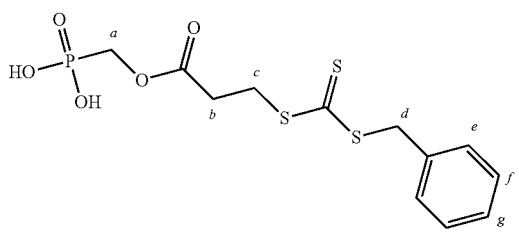 [SMILES: O=C(CCSC(=S)SCc1ccccc1)OCP(=O)(O)O]

$^1$H NMR (300 MHz, CDCl$_3$), δ (ppm form TMS): 2.8 (t, 2H), 3.6 (t, 2H), 4.4 (d, 2H) 4.6 (s, 2H), 7.2-7.4 (m, 5H)

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. An intermediate compound for forming a RAFT agent, the intermediate compound having the formula:

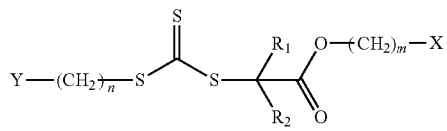

where n is an integer from 1 to 20; m is an integer from 0 to 20; R$_1$ is H, an alkyl group, or a cyano group; R$_2$ is H, an alkyl group, or a cyano group; Y is OH, COOH, or NH$_2$; and X is OH, COOH, NH$_2$, a nitrobenzyl, benzyl, or para-methyl benzyl group.

2. The intermediate compound of claim 1, wherein n is 2 to 10, and wherein Y is COOH.

3. The intermediate compound of claim 1, wherein R$_1$ is a methyl group, and wherein R$_2$ is a methyl group.

4. The intermediate compound of claim 1, wherein m is 2 to 10, and wherein X is OH.

5. The intermediate compound of claim 1, wherein the intermediate compound has the formula:

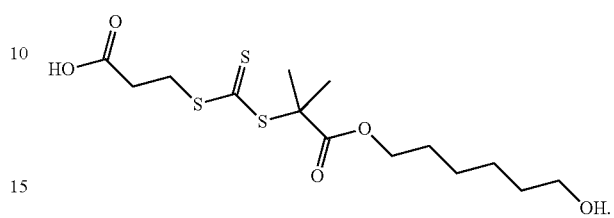

6. The intermediate compound of claim 1, wherein m is 0.

7. The intermediate compound of claim 1, wherein X is a benzyl ring.

8. The intermediate compound of claim 1, wherein the intermediate compound has the formula:

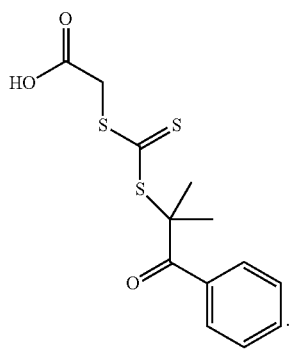 [SMILES: CC(C)(SC(=S)SCC(=O)O)C(=O)c1ccccc1]

9. A salt of the intermediate compound of claim 1.

* * * * *